United States Patent
Tonnel et al.

(10) Patent No.: US 9,102,658 B2
(45) Date of Patent: Aug. 11, 2015

(54) PROCESS FOR THE PREPARATION OF (5-FLUORO-2-METHYL-3-QUINOLIN-2-YLMETHYL-INDOL-1-Y1)-ACETIC ACID ESTERS

(71) Applicant: Atopix Therapeutics Limited, London (GB)

(72) Inventors: Jacques Tonnel, Elne (FR); Tony Pintus, Saint Jean de Linières (FR); Alain Burgos, Saint Genis-Laval (FR)

(73) Assignee: Atopix Therapeutics Limited, London (GB)

( * ) Notice: Subject to any disclaimer, the term of this patent is extended or adjusted under 35 U.S.C. 154(b) by 0 days.

(21) Appl. No.: 14/364,509

(22) PCT Filed: Dec. 14, 2012

(86) PCT No.: PCT/GB2012/000903
§ 371 (c)(1),
(2) Date: Jun. 11, 2014

(87) PCT Pub. No.: WO2013/088108
PCT Pub. Date: Jun. 20, 2013

(65) Prior Publication Data
US 2014/0350264 A1    Nov. 27, 2014

(30) Foreign Application Priority Data
Dec. 15, 2011 (GB) .................................. 1121557.1

(51) Int. Cl.
*C07D 401/06* (2006.01)

(52) U.S. Cl.
CPC .................................. *C07D 401/06* (2013.01)

(58) Field of Classification Search
CPC ........................... C07D 401/06; A01B 12/006
See application file for complete search history.

(56) References Cited

U.S. PATENT DOCUMENTS

| | | | |
|---|---|---|---|
| 7,582,672 B2 | 9/2009 | Middlemiss et al. |
| 7,750,027 B2 | 7/2010 | Armer et al. |
| 7,919,512 B2 | 4/2011 | Armer et al. |
| 7,999,119 B2 | 8/2011 | Armer et al. |
| 8,044,088 B2 | 10/2011 | Armer et al. |
| 8,163,931 B2 | 4/2012 | Middlemiss et al. |
| 8,163,936 B2 | 4/2012 | Middlemiss et al. |
| 8,168,673 B2 | 5/2012 | Armer et al. |
| 8,198,314 B2 | 6/2012 | Middlemiss et al. |
| 8,268,878 B2 | 9/2012 | Armer et al. |
| 8,314,257 B2 | 11/2012 | Middlemiss et al. |
| 8,536,158 B2 | 9/2013 | Armer et al. |
| 8,563,536 B2 | 10/2013 | Armer et al. |
| 8,703,956 B2 | 4/2014 | Betancourt et al. |
| 2007/0232681 A1 | 10/2007 | Middlemiss et al. |
| 2009/0186923 A1 | 7/2009 | Armer et al. |
| 2010/0022613 A1 | 1/2010 | Armer et al. |
| 2010/0041699 A1 | 2/2010 | Boyd et al. |
| 2010/0056544 A1 | 3/2010 | Lovell |
| 2011/0124683 A1 | 5/2011 | Hunter et al. |
| 2013/0052190 A1 | 2/2013 | Collins et al. |
| 2014/0039012 A1 | 2/2014 | Armer et al. |

FOREIGN PATENT DOCUMENTS

| | | |
|---|---|---|
| WO | 2006/092579 | * 9/2006 |
| WO | WO 2006/092579 A1 | 9/2006 |
| WO | 2007/107772 | * 9/2007 |
| WO | WO 2013/088108 A1 | 6/2013 |
| WO | WO 2013/088109 A1 | 6/2013 |

OTHER PUBLICATIONS

Appleton, J.E., et al., "A Mild and Selective C-3 Reductive Alkylation of Indoles," *Tetrahedron Letters* 34(9):1529-1532, Pergamon Press Ltd, England (1993).
International Search Report for International Patent Application No. PCT/GB2012/000903, mailed Feb. 12, 2013.

* cited by examiner

*Primary Examiner* — D M Seaman
(74) *Attorney, Agent, or Firm* — Sterne, Kessler, Goldstein & Fox PLLC

(57) ABSTRACT

The invention relates to a process for the preparation of a compound of formula (I) wherein $R^1$ is $C_1C_6$ alkyl or benzyl by reacting a compound of formula (II) wherein $R^1$ is as defined for formula (I) with 2-quinoline carboxaldehyde. The process is suitable for use on an industrial scale.

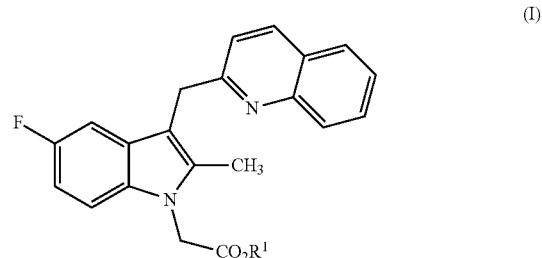

(I)

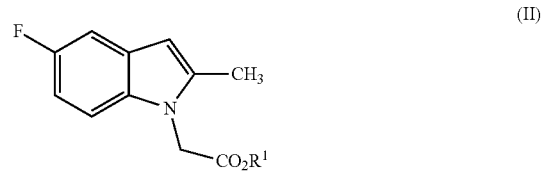

(II)

20 Claims, No Drawings

PROCESS FOR THE PREPARATION OF (5-FLUORO-2-METHYL-3-QUINOLIN-2-YLMETHYL-INDOL-1-YL)-ACETIC ACID ESTERS

The present invention relates to a process for the preparation of (5-fluoro-2-methyl-3-quinolin-2-ylmethyl-indol-1-yl)-acetic acid esters and in particular to a high yielding process which is suitable for use on an industrial scale.

WO 2005/044260 relates to compounds which are CRTH2 antagonists and which are therefore useful in the treatment of diseases and conditions mediated by the activity of PGD$_2$ at the CRTH2 receptor. One particularly useful compound disclosed in WO 2005/044260 is (5-fluoro-2-methyl-3-quinolin-2-ylmethyl-indol-1-yl)-acetic acid and several studies have been carried out on this compound, including clinical trials in man, which have demonstrated that it is effective in treating allergic rhinitis and asthma, especially eosinophilic asthma and atopic asthma.

(5-Fluoro-2-methyl-3-quinolin-2-ylmethyl-indol-1-yl)-acetic acid esters are intermediates in the preparation of (5-fluoro-2-methyl-3-quinolin-2-ylmethyl-indol-1-yl)-acetic acid. In addition, (5-fluoro-2-methyl-3-quinolin-2-ylmethyl-indol-1-yl)-acetic acid esters are useful as prodrugs for (5-fluoro-2-methyl-3-quinolin-2-ylmethyl-indol-1-yl)-acetic acid and are therefore useful in medicine.

(5-fluoro-2-methyl-3-quinolin-2-ylmethyl-indol-1-yl)-acetic acid was first described in WO 2005/044260 along with a number of other similar compounds. The document exemplifies a process for the preparation of {3-[1-(4-chloro-phenyl)-ethyl]-5-fluoro-2-methyl-indol-1-yl}-acetic acid and teaches that other compounds in the series were prepared by analogous methods.

According to Example 1 of WO 2005/044260, {3-[1-(4-chloro-phenyl)-ethyl]-5-fluoro-2-methyl-indol-1-yl}-acetic acid was prepared in the following steps:

i. (5-fluoro-2-methyl-indol-1-yl)-acetic acid ethyl ester and 4-acetylchlorobenzenze were reacted together in the presence of trifluoracetic acid and triethyl silane in the solvent 1,2-dichloroethane to give {3-[1-(4-chloro-phenyl)-ethyl]-5-fluoro-2-methyl-indol-1-yl}-acetic acid ethyl ester;

ii. the ester was hydrolysed using lithium hydroxide in a mixed tetrahydrofuran and water solvent to give the product.

WO 2006/092579 relates to a microcrystalline form of 5-fluoro-2-methyl-3-quinolin-2-ylmethyl-indol-1-yl)-acetic acid. This document teaches that the compound can be prepared according to the method shown in Scheme 1.

Scheme 1- Process for the Preparation of (5-fluoro-2-methyl-3-quinolin-2-ylmethyl-indol-1-yl)-acetic acid Stage 1

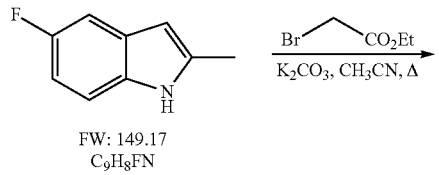

FW: 149.17
C$_9$H$_8$FN

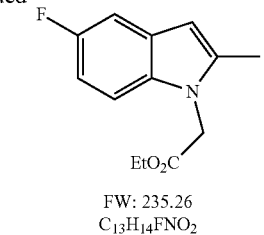

FW: 235.26
C$_{13}$H$_{14}$FNO$_2$

Stage 2

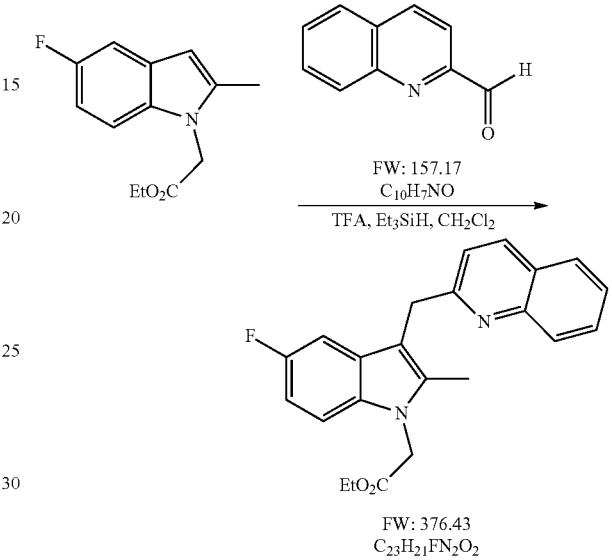

Stage 3

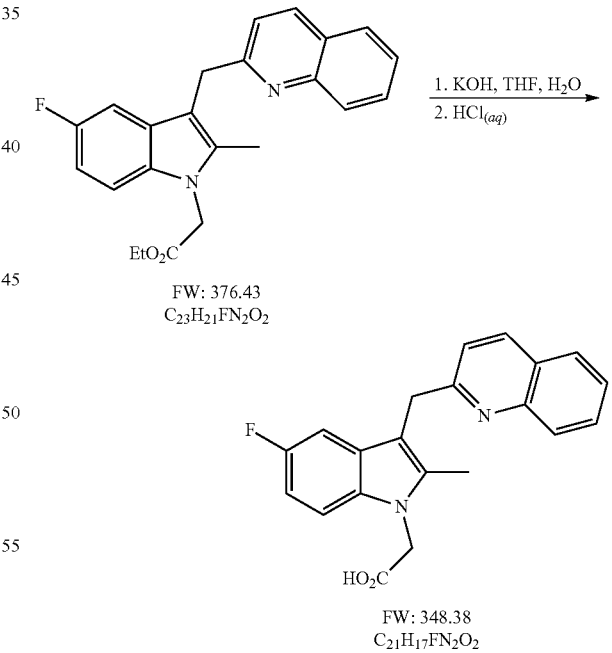

However, this process is a laboratory scale process and gives very modest yields of the target compounds. If (5-fluoro-2-methyl-3-quinolin-2-ylmethyl-indol-1-yl)-acetic acid is to be sold as a pharmaceutical, it is necessary to devise an economically viable process for its production on an industrial scale. Such a process must be high yielding and be capable of being operated at 100 kg scale or greater.

As can be seen from Scheme 1, the process of WO 2006/092579 is a three stage process. Stage 2 of the process is of particular interest as it is low yielding: Example 1 of WO 2006/092579 teaches that Stage 2, where (5-fluoro-2-methyl-indol-1-yl)-acetic acid ethyl ester was reacted with quinoline-2-carboxaldehyde, gave a product in 134% of the theoretical yield because the product was contaminated with silylated by-products. The products of both the Stage 2 process described in WO 2006/092579 and the Stage 2 process analogous to that described in WO 2005/044260 contain several impurities which are difficult to remove. Since (5-fluoro-2-methyl-3-quinolin-2-ylmethyl-indol-1-yl)-acetic acid is sparingly soluble in most solvents and is therefore difficult to purify by crystallisation, it would be highly advantageous if the precursor ester could be produced in a pure state.

Stage 2 of the process of Scheme 1 involves two different chemical reactions: firstly the reaction of the indole ester with quinoline carboxaldehyde under acidic conditions to give an intermediate alcohol (which is actually a racemic mixture of two enantiomeric alcohols); and secondly the reduction of the alcohol to give the required Stage 2 product as shown in Scheme 2.

Scheme 2- Stage 2 of the Process of Scheme 1

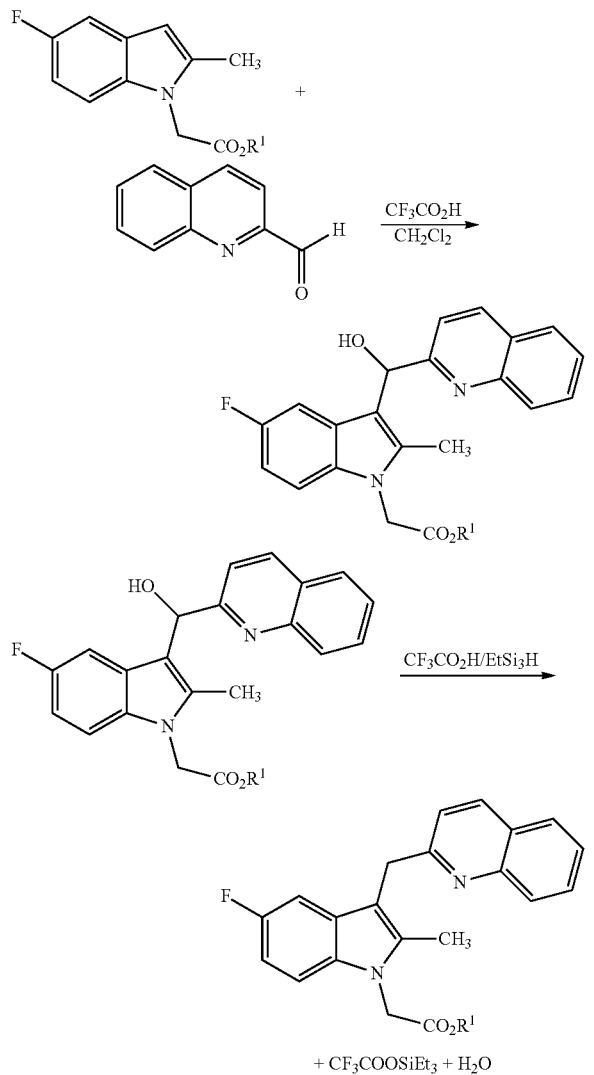

+ CF$_3$COOSiEt$_3$ + H$_2$O

In the process described in WO 2006/092579, these two processes are carried out in a single step in which the reducing agent triethyl silane and trifluoroacetic acid are sequentially added dropwise to a solution of the starting ester and 2-quinoline carboxaldehyde in dichloromethane at 0-5° C. and then 0-10° C.; following which the reaction mixture is stirred for 3 hours at reflux.

The procedure described in WO 2005/044260 is very similar and again both stages of the reaction are carried out in a single step. In this case, triethylsilane and trifluoroacetic acid are sequentially added dropwise to a stirred solution of (5-fluoro-2-methyl-indol-1-yl) acetic acid ethyl ester and the relevant aldehyde or ketone in 1,2,-dichloroethane at 0° C. The mixture is then allowed to warm to room temperature and stirred for 16 hours. In example 1 of WO 2005/044260, the yield of the product ester was only 37%.

However, the inventors have discovered that many of the problems associated with this method for conducting Stage 2 of the process arise from the low stability of the intermediate alcohol under the conditions described in WO 2005/044260 and WO 2006/092579 and the low reactivity of the intermediate alcohol towards the reducing agent.

The present inventors have investigated the properties of the alcohol and have developed an improved process for Stage 2 of Scheme 1.

Therefore, in the present invention, there is provided a process for the preparation of a compound of formula (I):

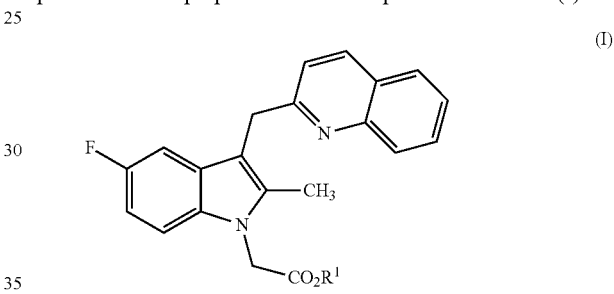

(I)

wherein R$^1$ is C$_1$-C$_6$ alkyl or benzyl;
the process comprising
i. reacting a compound of formula (II):

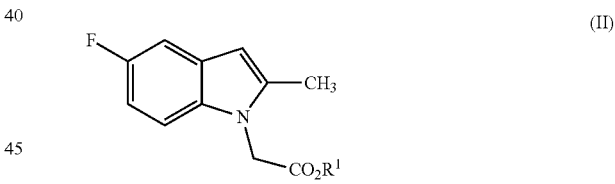

(II)

wherein R$^1$ is as defined for formula (I);
with 2-quinoline carboxaldehyde under acidic conditions and at a temperature of ≤10° C.;
to give an acid addition salt of a compound of formula (III):

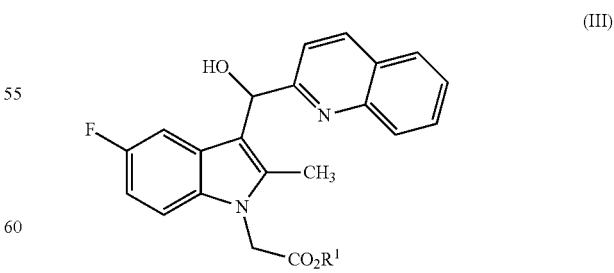

(III)

wherein R$^1$ is as defined for formula (I);
ii. when the reaction of step (i) is substantially complete, treating the acid addition salt with a base to obtain the alcohol of formula (III), while maintaining the temperature at ≤10° C.; and iii. reacting the compound of formula (III) with a reducing agent to give a compound of formula (I).

The process of the invention is much higher yielding than the process described in WO 2005/044260, with the yield being, in general, about 70-80% after step (iii).

Furthermore a purer product is obtained, which is important because the compound of general formula (I) is a pharmaceutical intermediate. Using the process of the invention, it is possible consistently to obtain a product of general formula (I) which contains total impurities at a level of ≤1.0% area by HPLC, with the amount of compound of formula (III) being present at ≤0.5% area (as the sum of the two enantiomers), and in some cases even lower than this.

As described above, the compound of general formula (I) is a precursor of carboxylic acids having CRTH2 antagonist activity. The intermediate of general formula (III) is very difficult to remove by crystallisation from the indole acetic acid product and therefore it is very important to minimise the amount of the compound of general formula (III) in the product of general formula (I).

In the process described above, where values for amounts of various compounds are expressed in terms of % area, this refers to the percentage of the area of the peak representing a particular molecule on an HPLC chromatogram. Thus, the product of general formula (I) contains total impurities at a level of ≤1.0% area by HPLC when the sum of the area of all the other peaks of the chromatogram is less than 1.0% of the total area of the HPLC chromatogram. The HPLC method by which the % area of the compounds of general formulae (I), (II) and (III) were determined in the process of the invention is described in detail in the Examples below.

In the process described above the group $R^1$ is generally $C_1$-$C_4$ alkyl, more usually methyl or ethyl and especially ethyl.

The reaction of step (i) may be carried out in an organic solvent, for example a halogenated solvent or an acetate such as ethyl acetate, an aromatic solvent such as toluene or acetonitrile or a combination of these. More suitable solvents include halogenated solvents such as dichloromethane or 1,2-dichloroethane, with dichloromethane being particularly suitable.

The acidic conditions required in step (i) may be provided by any acid, which may be either a Brønsted-Lowry acid or a Lewis acid but especially a strong acid. Trifluoroacetic acid (TFA) has been found to be particularly suitable. A strong acid such as TFA will generally be present in excess, for example a molar excess of ≥1.5 and more usually ≥2 moles of acid per mole of compound of formula (II).

As set out above, the reaction temperature for step (i) is ≤10° C. However, more suitably, the temperature is ≤5° C. and is usually about 0-5° C.

It is important to ensure that the reaction of step (i), is substantially complete before proceeding to step (ii). This is because any remaining compound of formula (II) present during step (iii), and the intermediate alcohol of formula (III) can also react to give a bis-indolyl compound which, in turn gives rise to a number of other impurities which are difficult to separate from the compound of formula (I). The yield of the compound of general formula (III) may be increased and thus the amount of residual compound of general formula (II) reduced by the use of a molar excess of 2-quinoline carboxyaldehyde in step (i). The number of equivalents of 2-quinoline carboxaldehyde is typically slightly in excess and, for example the number of equivalents of 2-quinoline carboxyaldehyde to compound of formula (II) may be about 1.05:1 to 1.5:1, typically about 1.1:1.

Since is important to ensure that the reaction of step (i) is substantially complete, i.e. that the amount of starting material remaining is minimal, before commencing the neutralisation process of step (ii), the amount of starting material remaining in the reaction mixture may be monitored, suitably by HPLC. It is well within the scope of a person of skill in the art to devise an HPLC method suitable for monitoring the reaction. The reaction of step (i) may be considered to be substantially complete when the amount of starting material of formula (II) remaining in the reaction mixture is ≤2% area by HPLC, more suitably ≤1.5% area by HPLC and particularly not greater than 1.0% area by HPLC. A suitable HPLC method for monitoring the reaction is described in the Examples below.

The product of step (i) is the acid addition salt of the intermediate alcohol of formula (III). For example, when TFA is used as the acid in step (i), the acid addition salt will be the trifluoroacetate salt.

The object of step (ii) is to obtain a neutral form of the compound of formula (III). The reason for this is that the compound of formula (III) is unstable under acid conditions and when attempts were made to carry out the reduction of step (iii) without a neutralising step, it was found that the compound of general formula (III) degraded and that various side products were obtained in significant amounts. The side products included an oxidation product—a ketone ester and various dimeric compounds.

The alcohol of formula (III) is stable under neutral conditions, however. Therefore, although the reduction of step (iii) is usually carried out under acid conditions, the alcohol of formula (III) is suitably added to the reduction mixture slowly, for example over several hours, so as to ensure that there is never an excess of the alcohol of formula (III). In this way, the degradation of the alcohol of formula (III) under the acid conditions used for the reduction step can be avoided. The major product is the desired product of formula (I) with only minor amounts of the ketone ester oxidation product and minimal amounts of dimeric impurities. In addition, the reaction proceeds much more rapidly.

It has been found that reduction of the neutral form of the alcohol of formula (III) proceeds more satisfactorily if the alcohol of formula (III) is substantially pure. Indeed, when a crude form of the alcohol of formula (III) is treated with triethylsilane, little reaction is observed after several hours of stirring at 0° C. When the temperature is increased to room temperature, the reaction yields mainly the ketone ester oxidation product; though small amounts of high molecular weight impurities are also present. However, no compound of formula (I) is obtained. In contrast, a purified form of the neutral alcohol of formula (III) reacts with a reducing agent such as triethyl silane under acid conditions as described above to give a high yield of the compound of formula (I) with only trace amounts of the ketone ester oxidation product and no other impurities. Furthermore, the reaction proceeds to completion and is thus very high yielding.

It is therefore important to ensure that the product of step (ii) is obtained in as pure a form as possible in order to ensure that step (iii) proceeds to completion and yields a pure product. Therefore, in order to obtain a substantially pure compound of formula (III), step (ii) may include the removal of impurities from the compound of formula (III).

In step (ii), the compound of formula (III) may be obtained from its acid addition salt by neutralisation of the reaction mixture. Any suitable base may be used in step (ii) to neutralise the compound of general formula (III) but typically an aqueous base is used, for example sodium, potassium or ammonium hydroxide. Aqueous potassium hydroxide has been found to be a particularly convenient choice of base as it is readily available at relatively low cost.

In this embodiment, removal of impurities may be achieved by washing the reaction mixture with water or an aqueous solution of, for example, an inorganic salt to remove any water soluble impurities remaining in the reaction mixture. This may be done before and/or after, but more suitably after, neutralisation of the reaction mixture.

In an alternative embodiment, the intermediate alcohol of general formula (III) may be isolated before proceeding to step (iii). Isolation of the alcohol may be achieved by removal of the acid salt product of step (i) from the reaction mixture, for example by filtration, when the reaction of step (i) is substantially complete. A person of skill in the art would be aware of a number of methods of monitoring the reaction in order to determine when it is substantially complete. One such method is HPLC and, as set out above, the reaction of step (i) may be considered to be substantially complete when the amount of compound of formula (II) remaining in the reaction mixture from step (i) is ≤1.0% area of the HPLC chromatogram. The isolated acid salt may then be treated with a base to give the free alcohol of general formula (III), which may be dissolved in an appropriate solvent for use in step (iii). Any suitable base may be used but typically an aqueous base is used, for example sodium, potassium or ammonium hydroxide, more usually aqueous sodium or potassium hydroxide. Aqueous potassium hydroxide has been found to be a particularly convenient choice of base as it is readily available at relatively low cost. Suitable solvents for step (iii) are described below.

In both embodiments, it is preferable to maintain a low temperature during the neutralisation and isolation and/or washing steps in order to avoid decomposition of the intermediate alcohol of formula (III) and/or to limit side reactions before the neutralisation is complete.

In step (iii), triethylsilane has been found to be a particularly suitable reducing agent and, in this case, the reaction is carried out under acidic conditions, for example in the presence of trifluoroacetic acid. Suitably, the reduction of step (iii) is carried out at the reflux temperature of the solvent, which is suitably a halogenated organic solvent such as dichloromethane or 1,2,-dichloroethane.

Other reduction methods may also be used, for example hydrogenation, typically using a metal catalyst such as palladium or platinum.

When triethylsilane is used as the reducing agent the molar ratio of triethylsilane to compound of formula (II) may be from 3:1 to 6:1, for example 3.5:1 to 5:1, suitably 4:1 to 5:1 and typically about 4.4:1. A triethylsilane reduction is usually carried out under acid conditions which may be provided, for example by the addition of trifluoroacetic acid, typically with excess reagent compared to the compound of general formula (II). For example, the number of equivalents of trifluoroacetic acid to compound of formula (II) may be from about 2:1 to 4:1, for example 2.9:1 to 3.5:1.

The reaction may be carried out under reflux and in the same solvent as for the previous steps. As mentioned above, it is important that the compound of formula (III) is added slowly to the reducing agent and therefore the addition will typically be carried out over several hours, for example about 4-10 hours, suitably 5-8 hours and more suitably about 6 hours.

Conveniently, in step (iii), the alcohol of formula (III) is added slowly to the reducing mixture. This avoids the build-up of the alcohol intermediate in the reaction mixture and lessens the chance of undesirable side reactions.

The compound of formula (III) is difficult to remove by crystallisation and therefore it is preferable to ensure that the reduction reaction of step (iii) proceeds to completion such that substantially no alcohol of general formula (III) remains before proceeding to work-up. As with the other reaction steps, the progress of the reaction can be monitored by any suitable method, for example a chromatography method such as HPLC, for example the method set out in the examples below. In step (iii), the reaction is substantially complete when not more than 0.5% area by HPLC alcohol remains before proceeding to work-up. In some cases, levels of alcohol lower than this may be achieved, for example ≤0.3, ≤0.25%, ≤0.2%, ≤0.15% or even ≤0.1% area by HPLC.

As set out above, step (iii) may be carried out using the solution of the compound of formula (III) obtained after neutralisation and, optionally washing with water.

In another embodiment, however, the alcohol of formula (III) is isolated and purified as described above before step (iii).

In a further aspect of the invention, there is provided an isolated and purified compound of formula (III) as defined above.

The process of the invention may include the additional step of:
(iv) isolating and purifying the compound of formula (I).

It has been found that most of the major impurities from the process can be removed from the reaction mixture simply by a work-up procedure involving aqueous washes followed by crystallisation.

Therefore, step (iv) of the process may comprise the step of washing the reaction mixture from step (iii) with water or an aqueous solvent to remove water soluble impurities after the reduction is complete.

Step (iv) may also comprise the step of crystallising the compound of formula (I) in a suitable solvent, typically a solvent such as ethanol or toluene or mixtures of these. Ethanol is a particularly suitable re-crystallisation solvent. The overall yield of the process including the crystallization step is generally about 65-70%.

As set out above, the compound of formula (I) is an intermediate in the production of (5-fluoro-2-methyl-3-quinolin-2-ylmethyl-indol-1-yl)-acetic acid and therefore in a further aspect the process of the invention includes the additional step of:
(v) converting the compound of formula (I) to (5-fluoro-2-methyl-3-quinolin-2-ylmethyl-indol-1-yl)-acetic acid, the process comprising hydrolysing the compound of formula (I).

Either acid or base hydrolysis of the compound of formula (I) may be used, although base hydrolysis is particularly suitable.

Typically, hydrolysis will be conducted in aqueous solution using a strong base such as lithium, sodium, potassium or ammonium hydroxide, more usually lithium, sodium or potassium hydroxide. Potassium hydroxide is, however, particularly suitable. Suitably the base will be a 50% aqueous potassium hydroxide solution.

The amount of base used is typically 1.5 to 4 molar equivalents of the compound of formula (I). Suitably, the molar ratio of base: compound of formula (I) is about 2:1.

Step (v) may be carried out at elevated temperature, for example 50 to 75° C., more usually 55° C. to 65° C. and typically about 60° C.

After hydrolysis is complete, the pH of the reaction mixture may be adjusted to about pH 6.5-7.5 in order to precipitate the product. If base hydrolysis has been used, the reaction mixture may be acidified using any suitable acid, for example mineral acids such as hydrochloric, sulphuric or phosphoric acids, organic acids such as formic acid or a similar aliphatic carboxylic acid. Hydrochloric and formic acids are particularly suitable for this purpose. The solid product may be isolated by any suitable process, for example filtration.

In addition, the process may optionally comprise the step of washing the reaction mixture with an organic solvent before acidification. Suitable solvents include, for example, chlorinated solvents such as dichloromethane and non-chlorinated solvents such as 2-methyltetrahydrofuran. This step is particularly useful for removing neutral or basic organic impurities which are not soluble in the potassium hydroxide solution. It has also proved useful for removing unreacted ester of general formula (I).

It has been found that, following the improvements to Stage 2 accorded by the process of the invention, the product of step (v) can be obtained in a form which is sufficiently pure for use as a pharmaceutical, so that further purification is unnecessary.

In order to obtain the starting material of general formula (II), the process may include additional steps before step (i).

Therefore, in a further aspect, the invention includes, before step (i), a process for the preparation of a compound of formula (II) comprising:

Reacting 5-fluoro-2-methyl indole with a compound of the formula (IV):

X—CH$_2$—COOR$^1$                                                      (IV)

where X is a leaving group, for example a halo group such as bromo and R$^1$ is as defined for formula (I).

The reaction may take place in the presence of a weak base such as potassium or caesium carbonate, more usually caesium carbonate, in a polar organic solvent such as acetonitrile.

Suitably the amount of solvent used is from 7 to 30 L of solvent per kg of 5-fluoro-2-methyl indole, more usually from 7 to 20 L, for example about 7 to 15 L and suitably about 10 L of solvent per kg of 5-fluoro-2-methyl indole.

The reaction may be conducted at a temperature of from about 15 to 30° C., more usually 20-25° C. over a time of 10 to 36 hours, typically 18 to 30 hours, for example about 24 hours and the progress of the reaction may be monitored, for example by a chromatography method such as gas chromatography (GC).

When the reaction is complete, the compound of formula (II) may be isolated and/or purified in order to remove impurities such as 5-fluoro-2-methyl indole and compound of formula (IV). Alternatively, purification of step (iv) may be sufficient. The presence of inorganic salts derived from the starting material of general formula (IV) is undesirable. Inorganic salts may be removed by washing the reaction mixture with water while maintaining the product of formula (II) in the organic phase. When a solvent such as acetonitrile is used as the reaction solvent, it may be advantageous to replace it at this stage with an alternative, less polar, solvent such as toluene.

The invention will now be described in greater detail with reference to the examples. In the examples, the following abbreviations are used:
TFA Trifluoroacetic acid
TES Triethyl silane
Et Ethyl
DCM dichloromethane In the examples set out below, and in the whole specification values for amounts of various compounds are expressed in terms of HPLC % area. This refers to the percentage of the area of the peak representing a particular molecule on an HPLC trace. The HPLC parameters are summarised below.

Column: YMC basic 150 mm×4.6 mm, 5 μm
Injection volume: 5 μL
Detection: UV @ 220 nm
Mobile Phase:
Mobile phase A: 0.1M ammonium formate pH 4.0:water:methanol (1:6:3)
Mobile phase B: 0.1M ammonium formate pH 4.0:methanol (1:9)
Gradient:

| Time (min) | % A | % B |
|---|---|---|
| 0 | 93 | 7 |
| 6 | 67 | 33 |
| 15 | 40 | 60 |
| 20 | 40 | 60 |
| 25 | 0 | 100 |
| 32 | 0 | 100 |
| 32.1 | 93 | 7 |
| 37.0 | 93 | 7 |

Flow rate: 1 mL/min
Temperature: 40° C.
Run time: 37 min (including a 5 min re-equilibration step)
Sample diluent: Acetonitrile
Quantification: % area

EXAMPLE 1

Investigation of Process of WO 2005/044260 for the Preparation of (5-fluoro-2-methyl-3-quinolin-2-ylmethyl-indol-1-yl)-acetic acid ethyl ester As illustrated in Scheme 2 above, Stage 2 of the process for preparing (5-fluoro-2-methyl-3-quinolin-2-ylmethyl-indol-1-yl)-acetic acid involves two chemical reactions: firstly the indole acetate reacts with quinoline carboxyaldehyde under acidic conditions to give the intermediate alcohol of formula (III); then the alcohol of formula (III) is reduced with TFA/TES. This is shown in the reaction scheme below, where R$^1$ is ethyl and the Stage 2 Product is (5-fluoro-2-methyl-3-quinolin-2-ylmethyl-indol-1-yl)-acetic acid ethyl ester.

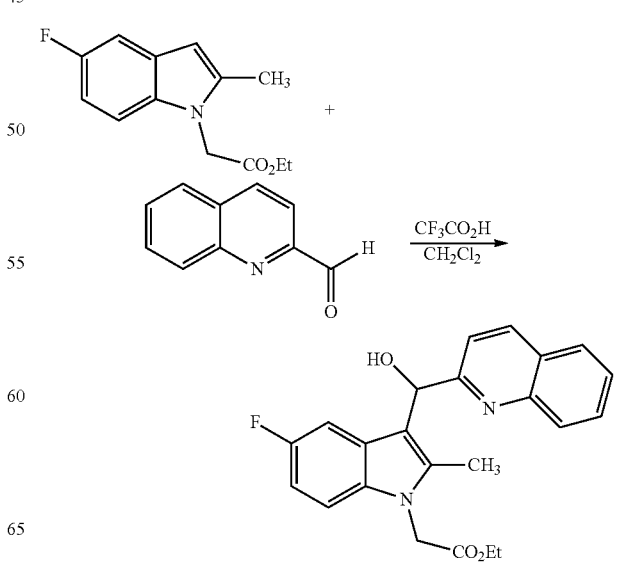

-continued

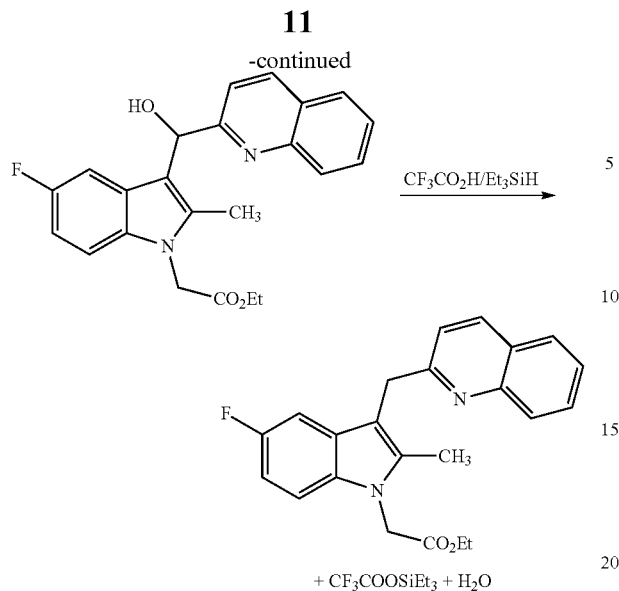

+ CF₃COOSiEt₃ + H₂O

According to the process described in WO 2005/044260, all the reagents except the TFA are added to the reaction vessel and then the acid is slowly added leading to the condensation of the indole acetate with the quinoline carboxaldehyde. The obtained alcohol is then slowly reduced.

We have discovered that the main problems with this procedure are related to the low stability of the intermediate alcohol at room temperature in acidic conditions and its low reactivity toward the TES reduction. When the reduction is performed according to the process of WO 2006/092579 or WO 2005/044260 (batch conditions); the intermediate alcohol is maintained for a long period of time at room temperature in acidic conditions leading to the formation of alcohol degradation impurities.

In order to circumvent this problem, alternative process implementation was studied.

Preparation of the Intermediate Alcohol of Formula (III)

This compound was easily prepared by slowly adding at about 0° C. the TFA (2 eq.) to a mixture of 5-fluoro-2-methyl-indole N-ethyl acetate (in 2 vols of toluene) and quinoline carboxaldehyde in methylene chloride. Despite the fact that this reaction is theoretically acid catalyzed, the use of less than 2 equivalents of TFA led to an incomplete reaction even after an extended reaction time.

The intermediate alcohol crystallized during the TFA addition or at the beginning of the holding time. The time of the crystallization can vary depending on the quality of the indole acetate charged (crude or pure) and on the amount of toluene in the crude indole acetate solution. The filtration of the suspension gave the alcohol in 79% yield. This isolated material contained 1 eq of TFA and was probably the salt of the alcohol.

The pure salt-free alcohol can be obtained by neutralization of the previously isolated material with diluted potassium hydroxide, extraction in methylene chloride and concentration.

Stability of the Intermediate Alcohol

Several studies were performed in order to determine the stability of this alcohol. Its behaviour was very different depending upon its purity, the temperature and the acidity of the mixture.

A. Pure Alcohol Isolated as a TFA Salt

At 0° C. in 9 vol. of DCM the pure alcohol (TFA salt) is not soluble and the mixture is a suspension. The reaction was monitored by HPLC which showed that the degradation is slow; leading mainly after 6 h of stirring to the formation of a dimer (1.7%), some ketone ester and some Stage 2 Product. The ketone ester has the structure:

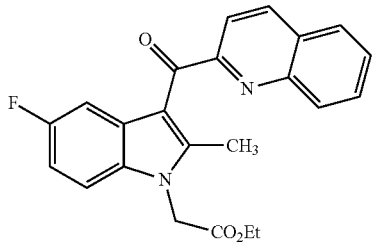 [SMILES: CCOC(=O)Cn1c(C)c(C(=O)c2ccc3ccccc3n2)c2cc(F)ccc21]

Increasing the amount of TFA (additional 1 equivalent) led to the full dissolution of the alcohol which degraded slightly faster leading, after 6 h to another dimeric impurity (2 to 3%) and some ketone ester+Stage 2 Product (2 to 3% each).

At room temperature, the pure alcohol (TFA salt) degraded more quickly leading after 6 h to the second dimeric impurity (5 to 6%), the ketone ester and the Stage 2 Product (8 to 10% each).

Increasing the amount of TFA led to a faster degradation with several late eluting impurities and small amounts of the ketone ester and the Stage 2 Product.

In conclusion, it appears that in acidic conditions (TFA) the alcohol degrades leading to a number of impurities in the window 25-28 minutes elution time (HPLC). Some ketone ester and Stage 2 Product may also be detected depending on the conditions. The rate of degradation increases with increasing temperature and increasing amount of TFA in the mixture.

B. Crude Alcohol Isolated as a Neutral Dichloromethane Solution

At 0° C., no change in the HPLC profile was observed after several hours of stirring.

At room temperature, after 16 hours the main impurity was the ketone ester (11%) but no Stage 2 Product was observed. Very small amounts of late eluting impurities were observed (<0.5% each) but interestingly, the peak of the remaining quinoline carboxaldehyde had disappeared. The repetition of this trial with some TES or under nitrogen gave the same result.

At higher temperature (70° C.) the degradation was much faster leading to the ketone ester (44% after 20 h) and the Stage 2 Product (26%). The presence of both ketone ester and Stage 2 Product suggests that in some conditions a disproportionation of the alcohol occurs.

C. Pure Alcohol Under Neutral Conditions

At room temperature in 10 vols of methylene chloride a 0.1% increase of the ketone ester content was observed after 16 h of stirring. Under reflux conditions (45° C.), HPLC showed an increase of about 1% of the ketone ester content after 18 hours. In both cases, no other impurity was detected.

In conclusion, it appears that in acidic conditions (TFA) the alcohol degrades leading to a number of impurities in the window 25-28 minutes elution time (HPLC). Some ketone ester and Stage 2 Product may also be detected depending on the conditions. The rate of degradation increases with increasing temperature and increasing amount of TFA in the mixture. The solubility of the alcohol might also play a role in the kinetic of degradation. At 0° C. with a low amount of TFA, a suspension is obtained, whereas with more TFA and/or higher temperature the mixture is a solution and the alcohol is more available to react.

Following these observations, we concluded that modification of the process described in WO 2005/044260 would be desirable in order to avoid extended stirring time of the alcohol in acidic conditions at room temperature. Certain variations of the process were therefore tested.

EXAMPLE 2

Investigation of Alternative Processes for the Preparation of (5-fluoro-2-methyl-3-quinolin-2-ylmethyl-indol-1-yl)acetic acid ethyl ester A. Charging a Mixture of Indole Acetate and Quinoline Carboxaldehyde onto TFA/TES This process modification is based on literature data (*Tet. Lett.*, 34, 1529 (1993). According to this publication, the indole derivatives and the aldehyde are mixed and charged to a cold mixture of TFA/TES. As we know that at low temperature the TES reduction of the alcohol is very slow we attempted to perform the addition in methylene chloride under reflux.

The yield and purity of reaction product from this approach was poor. The main impurity was the bis-indolyl compound of structure:

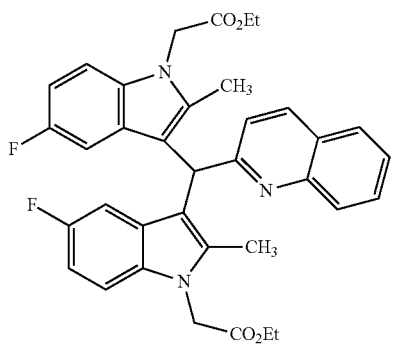 [SMILES: CCOC(=O)Cn1c(C)c(C(c2ccc3ccccc3n2)c2c(C)n(CC(=O)OCC)c3ccc(F)cc23)c2cc(F)ccc21]

(LC-MS identification) resulting from the reaction of the intermediate alcohol with the indole acetate. There is precedent in the literature for this behaviour (eg See A. Mahade_an et al. *I Tetrahedron Letters* 44 (2003) 4589-4591).

In addition to the bis-indolyl impurity there was also a significant amount of late eluting impurities and therefore this modification was not pursued. Running the reaction at 0° C. does not improve the profile but leads to a very long reaction time B. Addition of the Alcohol Suspension to the Reduction Mixture The alcohol salt (prepared as described in Example 1) was transferred to the reduction mixture (TFA/TES in DCM). Several trials were performed in order to determine the best reduction temperature and the transfer flow to limit alcohol accumulation in the reduction mixture. The experiments showed that the reduction mixture should be held under DCM reflux and the transfer time should not be less than 6 h.

Under these conditions the alcohol accumulation in the reduction mixture was low (less than 5 area %) so that the formation of the impurities was limited. The HPLC profile showed greater than 90% of Stage 2 Product. However the drawback of this procedure was the slow, flow-regulated transfer of a suspension. Moreover, even though the alcohol was found to be quite stable in these conditions, the impurities generated under acidic conditions were more difficult to remove than the ones generated under neutral conditions.

It was therefore decided to isolate the free alcohol as a DCM solution.

C. Transfer of the Alcohol as a Solution onto the Reduction Mixture

After the preparation of the intermediate alcohol, an aqueous work up (neutralization with potassium hydroxide followed by aqueous wash of the organic phase) led to a solution of the alcohol in DCM. This solution which was kept at 0° C. was then transferred onto the reduction mixture (TES/TFA at the reflux temperature of DCM). As described previously, this transfer was slow in order to avoid the accumulation of the alcohol. The solution was not dried as the alcohol is not stable at high temperature even under neutral conditions. The chemical purity at the end of the reduction was very similar compared to that obtained in B above.

D. Reaction with an Isolated Alcohol

Surprisingly, the pure isolated alcohol (III) underwent very fast (2 h) reduction to the Product (I) at room temperature. The chemical purity of the reaction mixture was also very high (>98%).

The following examples refer to a laboratory scale experimental protocol but were carried out on a larger scale.

EXAMPLE 3

Preparation of 5-fluoro-2-methyl-indole N-ethyl acetate (Stage 1)

Experimental Protocol

Into a reaction mixture of 1.0 Kg of 5-fluoro-2-methylindole (1.0 eq., 6.70 mol) and 0.99 kg of caesium carbonate (3.02 mol-0.45 eq.) with 9 L acetonitrile is added at 20-25° C. over ~12 h a solution of 1.34 kg ethylbromoacetate (8.04 mol-1.2 eq.) in 1 L acetonitrile. Two additional charges of 0.99 kg caesium carbonate each are added after 4 hours and after 8 hours of reaction (3.02 mol-0.45 eq.). A final charge of 0.33 kg caesium carbonate is added (1.01 mol-0.15 eq.) and 0.056 kg of ethyl bromoacetate (0.335 mol-0.15 eq.) are added after 18 hours. The reaction mixture is maintained under agitation at 20-25° C. until the reaction is substantially complete. 5 L of water is added to dissolve the inorganic salts. The agitation is maintained at 20-25° C. until complete dissolution of the inorganic salt then the reaction mixture is allowed to settle. The organic phase is concentrated to 3 L. Toluene (5 L) is added then the mixture is concentrated to 3 L. Toluene (5 L) is added to the reaction mixture; which is then washed with water (3 L) to eliminate the residual salts and concentrated to 3 L under vacuum. Expected Yield: 1.3-1.5 kg (90±5%).

Scaled Up Method

The above method was carried out with a batch size of 234 kg of 5-fluoro-2-methyl indole. The quantity of (5-fluoro-2-methylindol-1-yl)-acetic acid ethyl ester recovered was 337 kg, a yield of 91.3%; which compares well with the expected yield of 90±5%.

EXAMPLE 4

Preparation of (5-fluoro-2-methyl-3-quinolin-2-ylm-ethyl-indol-1-yl)-acetic acid ethyl ester (Process Stage 2)

Experimental Protocol 1.00 Kg of (5-fluoro-2-methylindol-1-yl)-acetic acid ethyl ester in 1.83 kg toluene is added to 0.73 Kg of quinoline carboxaldehyde (1.10 equivalents) and 6.0 L of methylene chloride. The solution obtained is cooled to a temperature below 5° C. and 0.97 Kg of TFA (2 equivalents) is added over approximately 2 h. Once the reaction is substantially complete, the suspension obtained is neutralized to pH=6-8, keeping the temperature below 5° C., by adding an aqueous solution of KOH of approximately 10% w/w. After settling, the organic phase, held at cool temperature, is separated and washed with 2.0 L of deionised water. The organic phase obtained is added over approximately 6 h to a solution of 2.17 Kg of triethylsilane (TES) (4.4 equivalents) with 1.50 Kg of trifluoroacetic acid (TFA) (3.1 equivalents) in 2.0 L of DCM at reflux.

After rinsing the vessel with 1.0 L with DCM, the reaction mixture is maintained at reflux until substantially complete. The solution obtained is cooled to 0-5° C. and 5.0 L of deionized water (5.0 vol) are added.

After settling, the aqueous phase is washed with 1.0 L of DCM and the pH of the combined organic extracts is adjusted to 6-7 with a solution of KOH (10% w/w) at a temperature of 0-5° C. When the desired pH is reached, 1.0 L of a solution of $K_2CO_3$ (25% w/w) is added and the biphasic mixture obtained is filtered through celite. After rinsing the equipment with 1.0 L of DCM, the mixture is allowed to settle and the aqueous phase is extracted with 2.0 L of DCM at 0-5° C. The combined organic phases are washed with 2×3.0 L of deionized water at 0-25° C.

The organic phase is concentrated at atmospheric pressure to a residual volume of 3.5 L, keeping the temperature below 80° C. After dilution with 3.5 L of ethanol, the mixture is concentrated at atmospheric pressure to a residual volume of 3.5 L keeping the temperature below 80° C. The reaction is again diluted with 3.5 L of ethanol and the mixture is concentrated at atmospheric pressure to a residual volume at 3.5 L keeping the temperature below 80° C.

After confirming the toluene content is not more than 5% w/w, the mixture is cooled to 0-5° C. then held at this temperature for 1 to 2 h. The mixture is then filtered and washed three times with 2.0 L of ethanol (pre-cooled to 0-5° C.). After confirming the residual silane content is not more than 1% w/w, the crude product is dried at 45° C. under vacuum.

The crude product is dissolved in 12 L of ethanol at reflux, clarified by filtration through celite at a temperature of not less than 65° C. and the equipment is rinsed with 1.0 L of ethanol at reflux (1.0 vol). The solution obtained is cooled to 60-65° C., seeded and held for 1 h at this temperature. The mixture is cooled to 0-5° C. and held at this temperature for 2 h. The suspension obtained is filtered and washed with 2×1.0 L of ethanol cooled to 0-5° C. then the product is dried under vacuum at 45° C. The weight of the dry product varied between runs from 1.04 to 1.28 Kg (65-80% Yield)

Scaled Up Method

The process described above has been scaled up to a batch size of 300 kg of (5-fluoro-2-methylindol-1-yl)-acetic acid ethyl ester. The recovered weight of crude (5-fluoro-2-methyl-3-quinolin-2-ylmethyl-indol-1-yl)-acetic acid ethyl ester was 359 kg. The corresponding yield is 74.8%.

The product was recrystallised from ethanol (12 volumes) with hot filtration through celite, at a temperature of not less than 65° C. The weight of product recovered was 334.4 kg—a yield of 93.1% for the re-crystallization step. The overall yield for the reductive alkylation was therefore 70%

EXAMPLE 5

Preparation of (5-fluoro-2-methyl-3-quinolin-2-ylmethyl-indol-1-yl)-acetic acid (Process Stage 3)

The product of Example 2 was hydrolysed to give 5-fluoro-2-methyl-3-quinolin-2-ylmethyl-indol-1-yl)-acetic acid using a procedure similar to that set out in WO2005/044260, which was as follows.

To 0.598 Kg of 50% aqueous potassium hydroxide (2 equivalents w.r.t. (5-fluoro-2-methyl-3-quinolin-2-ylmethyl-indol-1-yl)-acetic acid ethyl ester) is charged 9 L of purified water. Into this solution add 1 Kg of (5-fluoro-2-methyl-3-quinolin-2-ylmethyl-indol-1-yl)-acetic acid ethyl ester (2.656 Moles). The reaction mixture was heated to 60° C. and held until completion of the ester hydrolysis reaction. The reaction mixture is homogenous (solution is turbid) at the end of the reaction.

After work up, the product, (5-fluoro-2-methyl-3-quinolin-2-ylmethyl-indol-1-yl)-acetic acid was isolated and found to contain impurities in an amount of 1.5% area of an HPLC chromatogram. The yield for Stage 3 varied between about 91 and 99.5%.

The overall yield for Stages 1 to 3 of the process was 56%, substantially greater than that obtained using previous Stage 2 processes.

The invention claimed is:

1. A process for the preparation of a compound of formula (I):

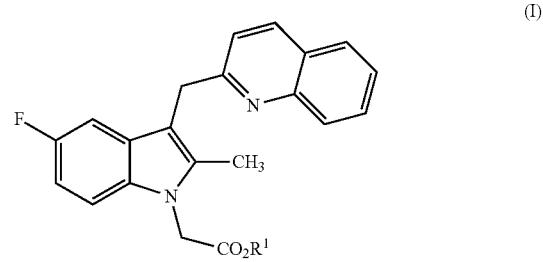

wherein $R^1$ is $C_1$-$C_6$ alkyl or benzyl;
the process comprising
i. reacting a compound of formula (II):

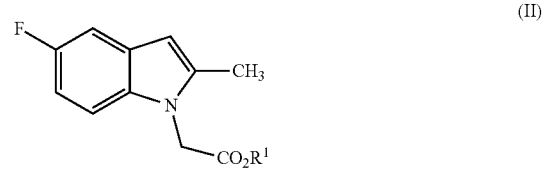

wherein $R^1$ is as defined for formula (I);
with 2-quinoline carboxaldehyde under acidic conditions and at a temperature of ≤10° C.;
to give an acid addition salt of a compound of formula (III):

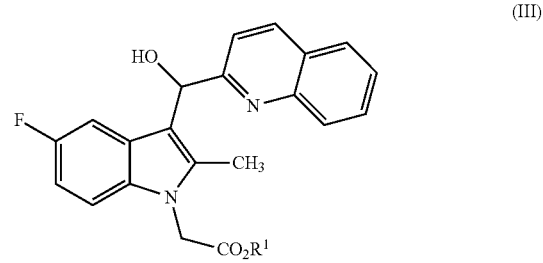

wherein $R^1$ is as defined for formula (I);
ii. when the reaction of (i) is substantially complete, treating the acid addition salt with a base to obtain the alcohol of formula (III), while maintaining the temperature at ≤10° C.; and iii. reacting the compound of formula (III) with a reducing agent to give a compound of formula (I).

2. The process according to claim 1 wherein $R^1$ is $C_1$-$C_4$ alkyl.

3. The process according to claim 2 wherein $R^1$ is ethyl.

4. The process according to claim 1, wherein the reaction of (i) is carried out in dichloromethane.

5. The process according to claim 1, wherein the acidic conditions in (i) are provided by trifluoroacetic acid (TFA).

6. The process according to claim 5 wherein the TFA is present in an amount of ≥2 moles of acid per mole of compound of formula (II).

7. The process according to claim 1, wherein the reaction of (i) is carried out at a temperature of about 0-5° C.

8. The process according to claim 1, wherein the molar ratio of 2-quinoline carboxyaldehyde to the compound of formula (II) is about 1.1:1.

9. The process according to claim 1 wherein (ii) includes the removal of impurities from the compound of formula (III).

10. The process according to claim 1 wherein, in (ii), the compound of formula (III) is obtained from its acid addition salt by neutralisation of the reaction mixture with a base; and optionally further comprising:
removing impurities by washing the reaction mixture with water or an aqueous solvent before and/or after neutralisation of the reaction mixture.

11. The process according to claim 1 wherein (ii) comprises
removing the acid salt product of (i) from the reaction mixture when the reaction of (i) is substantially complete; and
treating the isolated acid salt with a base to give the free alcohol of general formula (III).

12. The process according to claim 10 wherein the base is aqueous sodium or potassium hydroxide.

13. The process according to claim 1 wherein, in (iii) the reduction is carried out using triethyl silane.

14. The process according to claim 1 further comprising:
(iv) isolating and purifying the compound of formula (I); and optionally further comprising:
(v) converting the compound of formula (I) to (5-fluoro-2-methyl-3-quinolin-2-ylmethyl-indol-1-yl)-acetic acid, the process comprising hydrolysing the compound of formula (I).

15. The process according to claim 14, wherein the hydrolysis is base hydrolysis.

16. The process according to claim 1, further comprising before (i), preparing a compound of formula (II) by a process comprising:
reacting 5-fluoro-2-methyl indole with a compound of the formula (IV):

$$X-CH_2-COOR^1 \qquad (IV)$$

where X is a leaving group and $R^1$ is as defined for formula (I).

17. The process according to claim 16 wherein the reaction takes place in the presence of caesium carbonate in acetonitrile.

18. The process according to claim 16 wherein the amount of solvent is about 10 volumes of solvent per gram of 5-fluoro-2-methyl indole.

19. The process according to claim 16 further comprising isolating and purifying the compound of formula (II) before (i).

20. An isolated and purified compound of formula (III):

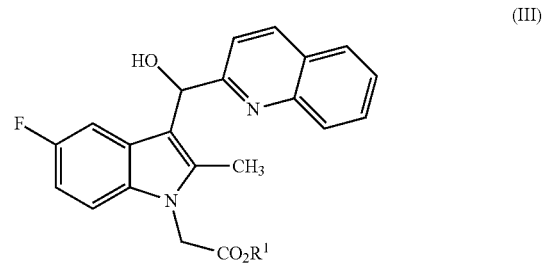

(III)

wherein $R^1$ is $C_1$-$C_5$ alkyl or benzyl.

* * * * *